United States Patent [19]

Elmqvist et al.

[11] Patent Number: 4,602,637

[45] Date of Patent: Jul. 29, 1986

[54] HEART PACEMAKER SYSTEM

[75] Inventors: Håkan Elmqvist, Bromma, Sweden; Konrad Mund, Uttenreuth, Fed. Rep. of Germany

[73] Assignee: Siemens Aktiengesellschaft, Berlin & Munich, Fed. Rep. of Germany

[21] Appl. No.: 569,979

[22] Filed: Jan. 11, 1984

[30] Foreign Application Priority Data

Jan. 11, 1983 [DE] Fed. Rep. of Germany ....... 3300672

[51] Int. Cl.⁴ .............................................. A61N 1/04
[52] U.S. Cl. ................................................ 128/419 P
[58] Field of Search .................... 128/419 P, 784–786

[56] References Cited

U.S. PATENT DOCUMENTS

| 3,735,766 | 5/1973 | Bowers et al. | 128/419 P |
| 4,010,759 | 3/1977 | Boer | 128/419 P |
| 4,011,861 | 3/1977 | Enger | 128/419 P |
| 4,033,357 | 7/1977 | Helland et al. | 128/785 |
| 4,248,237 | 2/1981 | Kenny | 128/419 P |
| 4,281,669 | 8/1981 | MacGregor | 128/419 P |
| 4,440,178 | 4/1984 | Bussard et al. | 128/784 |

FOREIGN PATENT DOCUMENTS

| 0043461 | 1/1982 | European Pat. Off. | |
| 2613072 | 10/1977 | Fed. Rep. of Germany | |
| 3203759 | 8/1983 | Fed. Rep. of Germany | 128/419 P |
| 2096001 | 10/1982 | United Kingdom | 128/419 P |

OTHER PUBLICATIONS

Guyton et al., "Theory and Design of Capacitor Electrodes for Chronic Stimulation" *Med. and Bio. Eng.*, vol. 12, No. 5, Sep. 1974, pp. 613–620.

Siemens–Elema brochure, "The Multiprogrammable Pulse Generator 668", Sep. 1979 (17 pages).

*Primary Examiner*—William E. Kamm
*Assistant Examiner*—Mitchell J. Shein
*Attorney, Agent, or Firm*—Hill, Van Santen, Steadman & Simpson

[57] ABSTRACT

Provided in order to avoid or at least reduce the problems produced by the passive electrode of a heart pacemaker system is a layer having a high double layer capacitance at the phase boundary with the bodily fluid. Advantageous to that end is a porous layer comprised of a carbide, nitride or carbonitride of at least one of the metals titanium, vanadium, zirconium, niobium, molybdenum, hafnium, tantalum or tungsten. The layer can also be comprised of activated carbon with a microporous exposed surface. The layer is produced in the simplest manner by means of roughening the existing electrode surface at its active area.

10 Claims, 3 Drawing Figures

HEART PACEMAKER SYSTEM

CROSS-REFERENCE TO RELATED APPLICATIONS

Reference is made to a copending application U.S. Ser. No. 569,832 filed Jan. 11, 1984 in the names of Konrad Mund, Helmut Freller and Friedrich Hoerauf, entitled "Electrode for Medical Applications" and to a copending application U.S. Ser. No. 569,980 filed Jan. 11, 1984 in the names of Lars Botvidsson and Konrad Mund, entitled "Bipolar Electrode for Medical Applications".

BACKGROUND OF THE INVENTION

The invention relates to a heart pacemaker system comprising at least one active electrode and one passive electrode, in particular the heart pacemaker housing. Such heart pacemaker systems are employed, among other things for bifocal stimulation and have, for example, an active electrode which is introduced after the implantation of the heart pacemaker into the atrium of the heart and a further active electrode that is inserted into the ventricle of the heart. Essentially two demands are made of implantable stimulating electrodes which generally are comprised of an insulated conductor and an electrode head connected to said conductor and having the active region:

(1) The electrode material must be compatible with the body so that the formation of connective tissue layers having a thickness greater than one hundred microns (100 μm) is suppressed so that the stimulation threshold remains largely constant.

(2) A high double layer capacitance should develop at the phase boundary electrode/body fluid so that the polarization rise during the stimulation pulses (0.5 through 1 ms, 1 Hz, 10 mA, 10 mm$^2$) remains less than 0.1 V.

These demands are met to a particularly high degree by electrodes wherein the active region consists of glassy carbon (v. German published application 2613072). A high double layer capacitance of up to 0.1 F/cm$^2$ is achieved due to an activation of the surface of the glassy carbon.

The only demand hitherto made of the passive electrode was that of compatibility with the body.

Given the said heart pacemaker system comprising two active electrodes and a shared passive electrode, problems can occur under certain conditions due to interactions between the electrodes. The cause thereof is a polarization rise at the passive electrode given stimulation with an active electrode. This polarization is slow to be dismantled and negatively influences the possibility of utilizing the other active electrode for detecting heart depolarizations during this time, since the polarization represents an increase of the electrochemical impedance of the system that makes the detection of the extremely small measurement currents considerably more difficult.

The functionability of the heart pacemaker system, further, can be negatively influenced by muscular convulsions. These muscle convulsions are generally based on the fact that the stimulation pulses not only stimulate the heart muscle but also stimulate stimulatable tissue in the proximity of the heart pacemaker housing which represents the passive electrode in the electrode system. The electrical voltage pulses associated with these muscle convulsions can simulate nonexistent heart activities under certain conditions. Previous attempts to eliminate this danger have been undertaken in that the heart pacemaker was surrounded by an insulating jacket. A hole through which the current can pass is situated in said jacket (SIEMENS-ELEMA brochure ME 372/5406.101, 1979). The heart pacemaker is then implanted such that the hole is situated at the side facing away from the stimulatable tissue. As a rule, the muscle convulsions stop.

In addition to these muscle convulsions, the problem also existed that the heart pacemaker could detect myopotentials of the skeletal musculature in the proximity of the heart pacemaker as depolarizations of the heart musculature. The danger of a negative influence on the heart pacemaker function as a result thereof also existed. This problem was also resolved by means of the insulating jacket and the proper placement of the heart pacemaker upon implantation.

This insulating jacket, however, also presents problems. First, the surface of the passive electrode is reduced, whereby the polarization effects increase and the efficacy of the stimulation pulses and the sensitivity of the heart pacemaker for detecting heart activities are reduced. On the other hand, problems regarding manufacture, hygiene and reliability arise due to this insulating jacket usually consisting of some kind or organic material.

SUMMARY OF THE INVENTION

It is therefore a principal object of the present invention to avoid or at least significantly reduce the problems produced in heart pacemaker systems of the type initially described due to the passive electrode and to increase the sensitivity of the electrode system at the same time.

This object is inventively achieved in that at least the active region of the passive electrode has a surface layer that provides a high double layer capacitance at the phase boundary with the bodily fluid. Thereby achieved, for example, is that the polarization rise upon stimulation is very slight. Given a bifocal system, therefore, stimulation can be carried out with one electrode and detection can be carried out with the other electrode with practically no loss of sensitivity.

It is also possible to leave the heart pacemaker housing conductive overall while yet serving as a passive electrode, i.e. to forego an insulating jacket. The surface hitherto left free of the insulation or a corresponding area is provided with the inventive surface layer and therefore exhibits a significantly lower electrochemical impedance relative to the surrounding tissue than does the remaining surface of the heart pacemaker housing. A voltage or, respectively, current division is thereby obtained. The area having the inventive surface layer will again be placed facing away from the stimulatable tissue or from tissues generating myopotentials when it is implanted.

It is particularly advantageous for the heart pacemaker system when, for example, the stimulation electrode and the passive electrode utilize the same material because material-associated potential differentials cannot occur in this case.

In an in vitro experiment, thus, a TiN stimulation electrode and two housing halves of the pacemaker fabricated of Ti were built into an electrolyte tank filled with 0.035M NaCl such that they simulated the heart pacemaker arrangement. Both housing halves were separately contacted and the sub-currents, given load with galvano-static pulses (I=10 mA, 1 ms), could be tracked via precision resistors. It turned out that the housing half facing the stimulation electrode is privileged at the beginning of the pulse and that the back housing half is more highly loaded after approximately 0.4 ms.

In the comparative experiment, the back housing part was provided with a six micron (6 μm) thick layer of porous TiN. It thereby turned out that the current is now preferentially carried by the back side after only 0.2 ms. Upon implantation, thus, this side should not contact any muscle tissue.

The inventive surface layer derives in a particularly simple fashion in that the conductive surface of the passive electrode—this is usually a matter, for example, of metallic materials such as platinum/iridium given heart pacemaker housings—is roughened in the active region. As a result of this roughening, the surface is quasi-enlarged by a multiple in comparison to a smooth surface layer, whereby a considerable increase of the double layer capacitance is already achieved. A further increase of the double layer capacitance is obtained in that the surface layer consists of activated carbon, in particular activated glassy carbon, as is already known for the electrode heads of the stimulation electrodes.

A surface layer that is particularly easy to manufacture and which is mechanically stable is formed by a porous layer consisting of a carbide, nitride or carbonitride of at least one of the metals titanium, vanadium, zirconium, niobium, molybdenum, hafnium, tantalum or tungsten.

The metals forming the carbides, nitrides and carbonitrides are all elements of the fourth through sixth sub-groups of the periodic system and thus include the so-called transition metals. Carbides MeC and nitrides MeN of the said type (Me=metal) are, for example, TiC, TiN, ZrC or TaN. The porous layer formed by such compounds has good conductivity and exhibits a thickness between one micron and one hundred microns (1 and 100 μm). Double layer capacitances that are of approximately the same magnitude as those of activated carbon thereby result. The manufacture of the layers, however, is considerably simpler. Tissue-compatible metals or metal alloys such as, for example, Eligiloy or, preferably, platinum and titanium serve as the carrier material for the layers.

In order to avoid the occurrence of mixed potentials, it can be provided in a further development of the invention that a tight nonporous layer which consists of the same material as the porous layer is situated between said porous layer and the carrier material. Under given conditions, it is thereby also possible to select a non-tissue-compatible material as the carrier material which is first surrounded with a tight nonporous layer of a tissue-compatible material that is then in turn coated with a porous layer of this same material, at least in the active region. The porous carbide, nitride or carbonitride layers are preferably applied to the carrier material serving as substrate by means of reactive ion plating, i.e. by means of physical vapor-deposition.

An exemplary embodiment of the inventive heart pacemaker system is described and explained in greater detail below with reference to a Figure of drawings; and other objects, features and advantages will be apparent from this detailed disclosure and from the appended claims.

DETAILED DESCRIPTION

Figure 1:
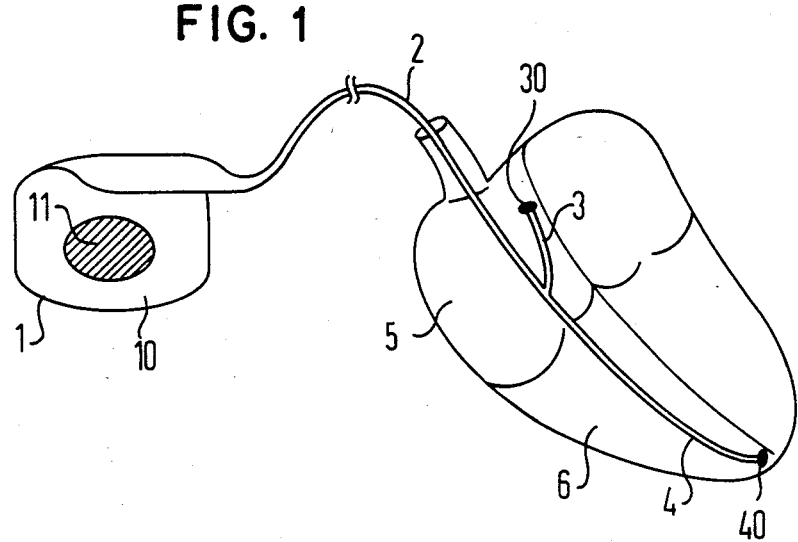
FIG. 1 schematically shows a system for bifocal stimulation of heart tissue constructed in accordance with the principles of the present invention.

The heart pacemaker system shown in FIG. 1 consists of the actual implantable heart pacemaker 1 having a closed housing 10 of, for example, titanium. An electrode line 2 for two stimulation electrodes 3 and 4 is shown connected to this heart pacemaker. The stimulation electrode 3 has an electrode head 30 which is provided for stimulating and sensing the heart activities in the left atrium 5 of a patient. The stimulation electrode 4 has an electrode head 40 which is correspondingly provided for the stimulation and detection of heart activities in the left ventricle 6.

Figure 2:
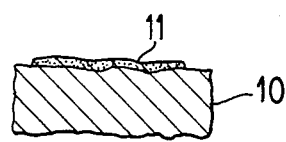
FIG. 2 is a schematic representation (not to scale) of the porous and non-porous layers in FIG. 1.

What is essential to this heart pacemaker system is that the housing 10 of the heart pacemaker 1 is provided with an area 11 at one side thereof having a porous layer of, for example, titanium nitride. Two effects become simultaneously possible as a result of this coating, as shown in FIG. 2. It will be understood the layer 11 differs in porosity from the housing material 10 only microscopically, and FIG. 2 is, thus, greatly exaggerated. First, the double layer capacitance between the housing 10 and the surrounding tissue (not illustrated) is greatly increased, whereby polarization effects are avoided. Second, the possibility of disposing the housing during implantation derives such that the layer 11 faces away from stimulatable tissue or from muscle tissue generating myopotentials so that the electrical pulses deriving therefrom are essentially suppressed and do not have a negative influence on the function of the heart pacemaker system.

Figure 3:
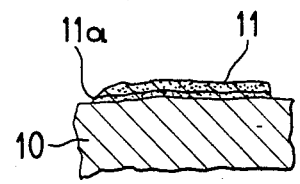
FIG. 3 is a schematic representation of a further embodiment having an additional non-porous sealing layer.

A further embodiment of the invention is shown in FIG. 3 wherein a tight non-porous layer 11a is disposed between the porous layer 11 and the housing carrier material 10. The non-porous layer 11a serves as a sealing layer, and consists of the same material as the porous layer 11. FIG. 3, as FIG. 2, is a schematic representation and is not to scale.

Elgiloy is a corrosion resistant alloy having the following components: cobalt, chromium, nickel, iron, molybdenum, manganese, carbon and beryllium.

A high double layer capacitance is a capacitance between the passive electrode at the active region and bodily fluid which permeates the active region which lies in the range from about ten millifarads per centimeter squared and about one hundred millifarads per centimeter squared when measured with a pulse repetition frequency of one hertz.

Titanium nitride-coated titanium sheets, for example, served for the determination of the electrochemical properties, having been investigated in a half cell arrangement with 0.15M NaCl as the electrolyte. A smooth platinum sheet served as cooperating electrode; an AgCl electrode was employed as the reference electrode. The electrodes were connected to a potentiostat and the potential values were converted and related to the potential of the reversible hydrogen electrode ($H_2$ electrode). The electrodes thereby set a potential of $\phi/H_{2\ rev} = 0.89$ V. (The specification $\phi/H_{2\ rev}$ denotes a potential referred to the reversible hydrogen electrode). Under potentio-dynamic load, with a voltage rate of change of ten millivolts per second (10 mV/s), one observed a constant current in the center of the interval $0 \leq \phi/H_{2\ rev} \leq 1$ V. Therefrom a double layer capacitance of 68 mF/cm$^2$ occurred at the beginning of the load, and this did not change over a load duration of eighty-eight hours (88 h). The investigations showed that no corrosion occurred up to a potential of 1.1 V; the electrodes are thus sufficiently stable.

The roughened surface layer at the active region 11 can be produced by roughening the exterior metallic surface of the wall of pacemaker housing 10 at active region 11 to provide at least twice the area of contact with bodily fluids as would be provided by a smooth metal surface of the housing 10 with a perimeter identical to that of the active region 11. The roughened surface 11 may be permeated by bodily fluids to a depth between about one micrometer (one micron) and about one hundred micrometers.

The active region 11 may also be comprised of activated carbon with a microporous exposed surface permeated by bodily fluids to a depth between about one micrometer (one micron) and about one hundred micrometers.

The term "mixed potentials" refers to potentials produced because of the presence of different materials—i.e. material associated potentials.

We claim:

1. A heart pacemaker system comprising a heart pacemaker having a metallic heart pacemaker housing, and at least one active electrode, the heart pacemaker housing having a region serving as a passive electrode, said region having a surface layer forming relatively high double layer capacitance at the phase boundary between said region and the surrounding body fluid, and a remainder of the pacemaker housing of substantial area forming a double layer capacitance with said surrounding body fluid substantially less than that of said region, said remainder being formed by an external metallic surface of said pacemaker housing which is exposed to the body fluid.

2. A heart pacemaker system as claimed in claim 1 wherein said surface layer provides a double layer capacitance between about ten millifarads per centimeter squared and about one hundred millifarads per centimeter squared as measured at a pulse repetition frequency of one hertz.

3. A heart pacemaker system as claimed in claim 1, wherein the surface layer is a roughened surface of limited extent of the metal wall forming the housing.

4. A heart pacemaker system as claimed in claim 1, wherein the surface layer consists of activated carbon overlying a portion of said metal wall forming said housing.

5. A heart pacemaker system as claimed in claim 1, wherein the surface layer is comprised of a porous layer of a material selected from the group consisting of a carbide, nitride or carbonitride of at least one of the metals titanium, vanadium, zirconium, niobium, molybdenum, hafnium, tantalum and tungsten, and wherein the metal wall forming the closed housing supports the surface layer and is comprised of a material selected from the group consisting of titanium and platinum.

6. A heart pacemaker system as claimed in claim 5, wherein the surface layer has a layer thickness between two and one hundred microns.

7. A heart pacemaker system as claimed in claim 6, further comprising a tight nonporous sealing layer of a material corresponding to the material of the porous layer disposed between the metal wall forming the housing and said porous layer.

8. A heart pacemaker system as claimed in claim 7, wherein the tight nonporous sealing layer has a layer thickness between two and ten microns.

9. A heart pacemaker according to claim 1, wherein said metallic pacemaker housing consists of titanium at its external surface except at said region, the surface layer being applied over the titanium of said housing coextensive with said region.

10. A heart pacemaker system according to claim 1, wherein said metallic pacemaker housing consists of platinum at its external surface except at said region, the surface layer being applied over the platinum of said housing coextensive with said region.

* * * * *